United States Patent
O'Donnell, Jr.

(10) Patent No.: US 6,271,028 B1
(45) Date of Patent: Aug. 7, 2001

(54) HEMATOPOIETIC CELL METHOD FOR TREATMENT OF HIV INFECTION

(76) Inventor: Francis E. O'Donnell, Jr., 709 The Hamptons La., St. Louis, MO (US) 63017

(*) Notice: Subject to any disclaimer, the term of this patent is extended or adjusted under 35 U.S.C. 154(b) by 0 days.

(21) Appl. No.: 08/910,084

(22) Filed: Aug. 12, 1997

Related U.S. Application Data

(60) Provisional application No. 60/023,250, filed on Aug. 12, 1996.

(51) Int. Cl.[7] ............... C12N 5/00; A61F 13/00; C12Q 1/70; G01N 33/53
(52) U.S. Cl. ............... 435/343.2; 424/422; 435/5; 435/7.24; 435/339.1; 435/372.3
(58) Field of Search ............... 435/5, 7.24, 339.1, 435/343.2, 372.3; 424/422

(56) References Cited

PUBLICATIONS

Fox, J. L., No winners against AIDS, Bio/Technology, vol. 12, p. 128, see entire page, Feb. 1994.*
Fahey et al., Status of immune–based therapies in HIV infection and AIDS, Clin. exp. Immunol. vol. 88, pp. 1–5, see p. 3, second column, third full paragraph, Jan. 1992.*

* cited by examiner

*Primary Examiner*—Hankyel Park

(57) ABSTRACT

The risk of drug resistance in HIV infection is reduced by profoundly suppressing the viral load using novel hematopoietic cells. Modified CD4 lymphocyte host cells are used to "capture" virions in a sterile micro-environment. The host's CD4 T-cell lymphocytes are replaced with lumphocytes derived from autologous or homologous stem cells which do not express the CKR-5 receptor, further inhibiting viral load.

11 Claims, 1 Drawing Sheet

HEMATOPOIETIC CELL METHOD FOR TREATMENT OF HIV INFECTION

CROSS-REFERENCE TO RELATED APPLICATION

This application claims priority on the provisional patent application filed Aug. 12, 1996, under Serial No. 60/023,250, of the same applicant.

FIELD OF INVENTION

The present invention relates to mammalian antiviral therapy. More particularly, it concerns the use of novel hematopoietic cells to reduce or eliminate human HIV infection.

BACKGROUND OF THE INVENTION

Recent advances in human HIV anti-retroviral therapy have included the development of powerful combinations of anti-retrovirals including nucleoside analogue and non-nucleoside analogue reverse transcriptase inhibitors used simultaneously with protease inhibitors. Nevertheless, the problem of de novo and, especially, acquired drug resistance is significant. Acquired drug resistance is now understood to be statistically more likely with greater viral load.

Prior art has identified that certain individuals are seemingly immune from HIV infection. These individuals seem to lack a normal CKR-5 co-receptor on the lymphocyte surface that must be assessed along with the CDR receptor for viral attachment.

Additional prior art has demonstrated the ability to use placental blood as a substitute for cross-matched donor stem cells in marrow transplants, and from prior art, we know that autologous human stem cells can be harvested and induced to reproduce in vitro.

Human retroviral infection with one of the variants of the HIV virus has been impossible to cure in vivo. In fact, antiviral pharmaceuticals have had limited success in retarding the infection and prolonging life. Despite a variety of pharmaceutical approaches, unfortunately, the virus has been able to develop drug resistance in each host, making it seemingly impossible to eradicate the viral infection and to control secondary infections such as CMV, retinitis, pneumocystis, pneumonia, etc.

SUMMARY OF THE INVENTION

The present invention reduces the viral replication process by using modified, novel hematopoietic cells. The multidrug antiviral and chemotherapy course can be used to eradicate the retroviral infection. Optimal time of therapy is disclosed and analyzed herein.

The pattern of emergent drug resistance in HIV infection is the result of the very high viral titers in advanced HIV infection—the acquired immunodeficiency syndrome (AIDS). Such high viral counts mean that drug resistance due to viral mutations is more likely. That is to say, the retroviral RNA mutation rate is roughly equivalent to other RNA and DNA mutation rates. But, in advanced HIV infection (AIDS), in particular, the number of replicating virions is in the billions, making it more likely statistically that drug resistance will emerge. In the hostile environment of systemic antiviral chemotherapy, the mutant virions will be "selected for." Thus, in the individual AIDS patient, the potential for drug resistance is very high.

This invention reduces the viral "battleground" to the micro-environment of a single cell by first designing a host cell that is devoid of the infrastructure or function necessary for viral replication. This host cell has the surface receptors (CD4) in a normal or even increased density required for retroviral incorporating into the host cell. These modified lymphocytes are used to "soak up" virions into a sterile environment during a multidrug regimen. By reducing the opportunity for drug resistant mutations, the present invention can be used to eradicate or significantly suppress the infection. Secondly, the present invention purposely eliminates or reduces the normal stem cell population which ultimately produces the lymphocytes susceptible to viral replication. The present invention repopulates the bone marrow with stem cells that produce lymphocytes lacking the CKR-5 receptors.

OBJECTS OF THE PRESENT INVENTION

It is an object of this invention to provide for modification of lymphocyte target cells to produce sterile ("drone") and/or hostile ("cruise") host cells that reduce the viral load to below 200 copies per $mm^3$ when infused to a concentration of 1,000 to 1,000,000 or more cells per $mm^3$ and thereby mitigate the chances of emergent drug resistance during the course of antiviral treatment for retrovirus infection.

Another object of this invention is to provide a lymphocyte target cell of the type as just previously described wherein the cellular mechanisms required for viral replication are inactivated or deleted ("drone" lymphocyte).

Another object of this invention is to provide a lymphocyte target cell wherein its pretreatment with a multidrug array of antivirals substantially diminishing ability of the virus to replicate ("cruise" lymphocytes), particularly after the cellular mechanisms have been treated to inactivate or delete viral replication.

Another object of this invention is to provide for an isolation of autologous lymphocytes through the use of leukophoresis techniques for the purpose of mitigating the chances of emergent drug resistant virus during the course of antiviral treatment for retrovirus infection.

Yet another object of this invention is to provide the method for harvesting of lymphocytes for their modification through the use of the process of this invention wherein the lymphocytes may be stored for future usage.

Another object of this invention is to provide for the periodic use of leukophoresis to remove spent modified lymphocytes and to replenish the count of modified lymphocytes generated in accordance with this invention.

Yet another object of this invention is to provide the method for timing of intervention of the principal method of this invention as previously described, preferably before a significant reduction in CD4 T-cell count.

Another object of the present invention is to reduce or eliminate lymphocytes susceptible to HIV replication by repopulating the marrow with modified stem cells which do not express the CKR-t receptor on their derivative lymphocytes.

DESCRIPTION OF THE PREFERRED EMBODIMENT

Figure 1:
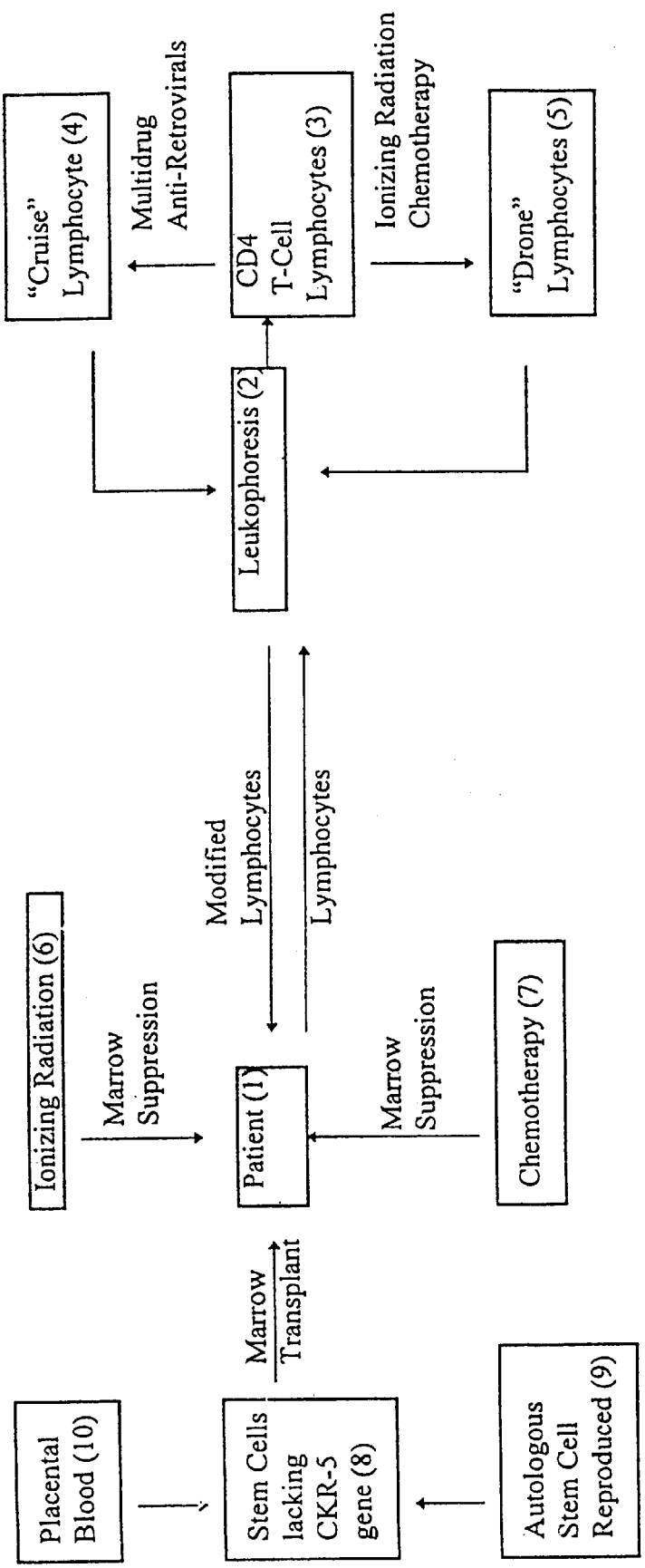
FIG. 1 is a description of leukophoresis (2) is used to isolate T-cells (lymphocytes) (3) for treatment with radiation means such as gamma radiation to inactivate the cellular infrastructure for viral replications creating "drone" lymphocytes (5) and/or with means for incubating with a multi-drug array of anti-HIV agents creating "cruise" lymphocytes before reintroducing these modified T-cells back into the patient.

The HIV-infected patient with high viral loads and/or drug resistance (1) is rescued by leukophoresis (2) removal of white blood cells, and more particularly, CD4 T-cell lymphocytes (3), allowing for creation of "cruise" lymphocytes (4) and/or of "drone" lymphocytes (5). These modified lymphocytes are returned to the patient through the leukophoresis process (2). The patient's normal population of susceptible lymphocytes is reduced by ionizing radiation (6) and/or chemotherapy (7) aimed at making the marrow aplastic. As part of the rescue therapy, stem cells lacking the CKR-5 gene or its normal expression (8) are transplanted to the marrow. These stem cells can be autologous (9) after undergoing in vitro reproduction and gene therapy or they can be homologous (10) derivatives of placental blood after undergoing in vitro gene therapy to eliminate the CKR-5 receptors.

In one preferred embodiment, "drone" lymphocytes are created by leukophoresis (FIG. 1) removal of the patient's own lymphocytes. These autologous lymphocytes are treated with gamma radiation, ultraviolet light and the like in order to render their cytoplasmic and nuclear mechanism incapable of supporting viral replication.(FIG. 1).

In another preferred embodiment, the unaltered or altered, "drone" lymphocytes are treated in vitro with a multidrug array of antivirals; for example, such as a protease inhibitor, reverse transcriptase inhibitor, and nonsense nucleoside. These "cruise" lymphocytes feature an intracytoplasmic environment that is further hostile to the invading virions. In the individual host cell, such a multidrug load makes it very unlikely that drug resistance will emerge (FIG. 1). Moreover, concentrations of the antivirals intracellularly can be achieved in vitro that would be toxic if given in vivo systemically.

In another preferred embodiment, the T-cells of the present invention are incubated in vitro with a solution of cell surface receptors (CD4) in order to increase the ability of virus to gain access to the modified lymphocytes.

In another preferred embodiment, the isolated, autologous lymphocytes are stored for infusion into the patient at a later time. In this way, the patient with depressed host cells can provide sufficient material to create "drone" and "cruise" lymphocytes.

In order to provide sufficient reduction in viral load, the modified lymphocytes ("drone" and "cruise") may need to be given in a count from $1,000^3$ to $1,000,000$ or more $mm^3$, depending in part upon the patient's count of infected lymphocytes. That is to say, the greater the viral load or the greater the percentage of infected lymphocytes, the larger the number of modified lymphocytes necessary to reduce the viral load.

In another preferred embodiment, the leukophoresis process can be repeated at regular intervals to remove the old "drone" and "cruise" lymphocytes from the patient.

In another preferred embodiment, the intervention of this invention is instituted before the viral load becomes sufficient to suppress the lymphocyte count (CD4 T-cells) significantly. In this way, the viral load represents a much smaller number, making it more likely statistically to avoid drug resistance during antiviral therapy.

In another preferred embodiment, the patients undergo chemotherapy designed to eradicate their stem cells. They are then "rescued" by marrow transplants from matched donors, wherein the donor cells are pre-treated with a multidrug array of antivirals.

In another preferred embodiment, patients are treated with chemotherapy after their marrow cells have been harvested. Their marrow cells are pre-treated with a multidrug array of antivirals before autotransplantation.

In another preferred embodiment, the normal population of susceptible CD4 T-cell lymphocytes can be reduced or eliminated. Ionizing radiation or alkylating chemotherapy can be used to make the marrow aplastic. The marrow is then repopulated with autologous stem cells or homologous stem cells from placental blood. In either instance, gene therapy pre-treatment can be done to block expression of the CKR-5 receptor in the derivative CD4 T-cells. In the case of placental blood, preference is given to donor material which naturally lacks expression of the CKR-5 receptor.

Variations or modifications in the method of treating viral contaminated cells may occur to those skilled in the art upon reviewing the summary of the invention, in addition to its preferred embodiments. Such variations, if within the spirit of this invention, are intended to be encompassed within the scope of the disclosure provided herein.

I claim:

1. A method of preparing host cells that are substantially devoid of infrastructure required for viral replication which comprises:
   (a) isolating mononuclear target cells from a host;
   (b) performing in vitro treatment of the target cells with a multi-drug array of antivirals and/or ionizing radiation chemotherapy to render the target cells' replicative infrastructure substantially ineffective; and
   (c) harvesting the resulting autologous lymphocytes and lymphocytic stem cells.

2. The method of claim 1 wherein the lymphocytes are isolated by leukophoresis.

3. The method of claim 1 wherein the lymphocytes are harvested and stored in vitro.

4. The method of claim 1 wherein the autologous lymphocytes and lymphocytic stem cells are treated through the use of chemotherapy to reduce any virile replication.

5. The method of claim 1 wherein the autologous lymphocytes and lymphocytic stem cells are treated through the use of a multi-drug array of antivirals.

6. The method of claim 5 wherein the stem cells lack CKR-5 genes.

7. The method of claim 5 wherein the target cells are CD4 target cells.

8. The method of claim 5 wherein protein synthesis in the target cells is blocked by pretreatment of the cells with a pharmacologic inhibitor of protein synthesis.

9. The method of claim 1 wherein the in vitro treatment of the target cells is performed in a solution containing surface receptors.

10. The method of claim 1 wherein the ionizing radiation is gamma radiation or ultraviolet light radiation.

11. The method of claim 1 wherein the multi-drug array comprises at least a protease inhibitor, or a reverse transcriptase inhibitor, or a nonsense nucleoside.

* * * * *

UNITED STATES PATENT AND TRADEMARK OFFICE
CERTIFICATE OF CORRECTION

PATENT NO.     : 6,271,028 B1                                              Page 1 of 1
DATED          : August 7, 2001
INVENTOR(S)    : O'Donnell, Francis E., Jr.

It is certified that error appears in the above-identified patent and that said Letters Patent is hereby corrected as shown below:

<u>Column 4, claim 8,</u>
Line 1, change "5" to -- 1 --.

Signed and Sealed this

Sixteenth Day of April, 2002

Attest:

JAMES E. ROGAN
*Attesting Officer*            *Director of the United States Patent and Trademark Office*